United States Patent [19]

Musacchio et al.

[11] Patent Number: 4,870,024
[45] Date of Patent: Sep. 26, 1989

[54] CONCURRENT ANALYSIS OF A FLUID SAMPLE FOR CALCIUM AND A MONOVALENT ION

[75] Inventors: John Musacchio, Tyngsboro; Carolyn Bergkuist, Hampstead, both of Mass.; Angelo Manzoni, Milan, Italy; Pietro Premoli, Vercelli, Italy

[73] Assignee: Fisher Scientific Company, Pittsburgh, Pa.

[21] Appl. No.: 74,881

[22] Filed: Jul. 17, 1987

[51] Int. Cl.$^4$ ............................................. G01N 27/46
[52] U.S. Cl. ...................................... 436/74; 204/1 T; 204/400; 422/68; 436/79; 436/151; 436/164
[58] Field of Search .................. 436/74, 79, 151, 164; 204/1 T, 400; 422/68

[56] References Cited

U.S. PATENT DOCUMENTS 4,618,587 10/1986 Premoli ............................... 436/74

FOREIGN PATENT DOCUMENTS 166944 1/1986 European Pat. Off. .

OTHER PUBLICATIONS

Anker, Peter, *Anal. Chem.* "Neutral Carrier Based Ion-Selective Electrode for the Determination of Total Calcium in Blood Serum", vol. 53, No. 13, pp. 1970–1974 (Nov. 1981).
Allied Instrumentation Laboratory, "IL Test ISE Buffer", Cat. No. 351297-10, (Mar. 1985).
Nova 7, "Total Calcium/Ionized Calcium/pH".

*Primary Examiner*—Barry S. Richman
*Assistant Examiner*—Jill Johnston

[57] ABSTRACT

A method for determining the concentrations of total calcium and at least one monovalent ion in a sample includes the steps of mixing the sample with a diluent that has a pH within the range pH 6.5 to 7.0 and includes 2-amino-2-hydroxymethyl-1,3-propanediol phosphate and is free of the monovalent ion. An aliquot of the diluted sample is concurrently contacted with a calcium-specific ion selective electrode and an ion selective electrode specifically responsive to the monovalent ion, the response of the calcium-specific ion selective electrode is measured as an indication of the concentration of total calcium in the sample, and the response of the monovalent ion specific ion selective electrode is measured as an indication of the concentration of the monovalent ion in the sample.

21 Claims, No Drawings

CONCURRENT ANALYSIS OF A FLUID SAMPLE FOR CALCIUM AND A MONOVALENT ION

BACKGROUND OF THE INVENTION

This invention relates to measuring total calcium in biological samples.

In biological samples, calcium ions are present either as free ions or bound to sample components such as proteins. To determine the calcium content of the sample accurately, it is necessary to measure the contributions from both forms (i.e. the "total calcium").

Total calcium has been measured colorimetrically using an acidic indicator dye, e.g., cresolphthalein complexone, whose color is sensitive to calcium ion concentration and which releases bound calcium ions. Dye and buffer solution are added to the sample separately (2 point calibration method) or combined and added together (1 point calibration method). In the latter method, the dye buffer reagent must be used within a short period of time following combination because the dye has only limited stability in the alkaline environment of the buffer solution.

Colorimetric measurement of total calcium is not compatible with the measurement of monovalent ions, e.g., sodium, potassium, or chloride because these ions cannot be measured colorimetrically.

Another way of measuring total calcium has been to use atomic absorption spectroscopy (AAS). AAS, however, is too expensive and time consuming for routine sample analysis.

Total calcium has also been measured using an ion sensitive electrode containing a calcium ionophore. In one such method, the sample is treated with a dilute acidic solution (pH=4.0 to 5.5) to release bound calcium. The calcium ionophore then binds the released ions, thereby changing the electrode's output voltage; the change is related to the calcium ion concentration. Because sodium ions cannot be measured accurately at pH values less than 6.0, this method of measuring calcium is incompatible with measurement of sodium ions. Moreover, conventional calcium ionophores are unstable in acidic conditions (pH<6) because they hydrolyze and thereby lose their ability to bind calcium ions, a special chemically modified calcium ionophore that is stable under acidic conditions is used in such known methods.

SUMMARY OF THE INVENTION

In general, the invention features a method for determining the concentrations of total calcium and at least one monovalent ion in a sample which may contain protein-bound calcium, the method including the steps of admixing the sample with a diluent, the diluent comprising 2-amino-2-hydroxymethyl-1,3-propanediol phosphate and having a pH within the range pH 6.5 to pH 7.0 and being free of the monovalent ion. An aliquot of the diluted sample is contacted with a calcium specific ion selective electrode and an ion selective electrode specifically responsive to the monovalent ion, the response of the calcium specific ion selective electrode is measured as an indication of the concentration of total calcium in the sample, and the response of the monovalent ion specific ion selective electrode is measured as an indication of the concentration of the monovalent ion in the sample.

Preferably, the monovalent ion is sodium, potassium, or chloride, and in a particular embodiment, the diluent is free of ions of calcium, sodium, potassium and chloride. Preferably, the diluent further comprises a reducing agent and a surfactant, and in a particular embodiment, the reducing agent is an aldehyde and the surfactant is non ionic. Preferably, the volume to volume ratio of the sample to the diluent is between 1:30 and 1:60, and the concentration of the 2-amino-2-hydroxymethyl-,1,3-propanediol phosphate in the diluent is at least 0.1 millimol per liter.

In a preferred process, the calcium specific ion selective electrode and the monovalent responsive ion selective electrode are contacted with a reference solution that has the same chemical composition as the diluent except that the reference solution also contains calcium ion and the monovalent ion sources.

The invention provides a simple, effective, inexpensive method for concurrently measuring the concentration of total calcium, sodium, chloride, and potassium in a biological sample, e.g., serum or urine. Accurate total calcium measurements are obtained using only a single reagent (the diluent). Because the diluent is stable, it can be conveniently stored for long periods of time. In addition, because its pH is in the 6.5-7.0 range, it does not hydrolyze the calcium ionophore of the ion sensitive electrode. Thus, conventional commercially available electrodes, rather than special chemically modified electrodes, can be used. Furthermore, a single aliquot of the sample can be analyzed for both calcium and monovalent ions (e.g., sodium, potassium, and chloride) because the diluent does not interfere with the monovalent ion measurements.

Other features and advantages of the invention will be apparent from the following description of the preferred embodiments thereof, and from the claims.

DESCRIPTION OF PARTICULAR EMBODIMENT

The sample diluent for measuring total calcium includes a transfer agent, 2-amino-2-hydroxymethyl-1,3-propanediol (tris base), capable of rendering calcium that is bound to sample components freely available for detection by a calcium ionophore containing electrode. The term "transfer agent" reflects a belief that the transfer agent reversibly binds calcium ions in the pH range 6.5 to 7 and thus effectively "transfers" the calcium ions from the sample components to the calcium ionophore on the electrode. The transfer agent contains one or more heteroatoms (i.e. nitrogen, oxygen, or sulfur atoms) having unpaired electrons that confer calcium binding ability on the transfer agent. The transfer agent can be provided in neutral (i.e. uncharged) form or in the form of a salt in which the heteroatom is positively charged (e.g., tris phosphate).

A single aliquot of a sample of, e.g., urine or serum can be concurrently analyzed for total calcium, sodium, potassium, and chloride ions in an analyzer of the type disclosed in copending application Ser. No. 074,942 entitled LIQUID HANDLING (Case 316) filed concurrently herewith, the disclosure of which is specifically incorporated by reference. When chloride ions are being measured it is desirable to include a reducing agent (preferably one or more aliphatic aldehydes) and a surfactant (preferably a nonionic surfactant) to the transfer solution to minimize interaction of protein with the chloride electrode. The use of a nonionic surfactant with tris phosphate, also improves calcium ion transfer.

The transfer solution can also contain stabilizers and microbicides to extend its shelf life.

The sample diluent (pH 6.8) has the following chemical composition

| | |
|---|---|
| 2-amino-2-hydroxymethyl-1,3-propanediol (tris base) | 0.15 M |
| Phosphoric Acid | 4.8 ml/l |
| Crotonaldehyde | 0.49 ml/l |
| Acetaldehyde | 0.90 ml/l |
| Nonionic surfactant (Polysorbate 20 - TWEEN ™ 20) | 1.0 g/l |
| Stabilizer (Dimethoxane-Giv-Gard ™ DXN, $C_8H_{14}O_4$) | 2.0 g/l |

A reference solution used to calibrate the ion selective electrodes has the following chemical composition:

| | |
|---|---|
| 2-amino-2-hydroxymethyl-1,3-propanediol (tris base) | 0.15 M |
| Phosphoric Acid | 4.8 ml/l |
| Calcium Nitrate | 0.0147 g/l |
| Sodium Chloride | 0.158 g/l |
| Potassium Chloride | 0.0107 g/l |
| Sodium Sulfate | 0.0913 g/l |
| Crotonaldehyde | 0.49 ml/l |
| Acetaldehyde | 0.90 ml/l |
| Nonionic surfactant (Polysorbate 20-TWEEN ™ 20) | 1.0 g/l |
| Stabilizer (Dimethoxane DXN, $C_8H_{14}O_4$) | 2.0 g/l |

The chemical composition of the sample diluent is identical to that of the reference solution except that the reference solution also contains calcium nitrate, sodium chloride, potassium chloride, and sodium sulfate, as ion sources for calibration of calcium ion, sodium ion, potassium ion and chloride ion, respectively.

The concentrations of calcium, sodium, potassium, and chloride ions in a urine or serum sample are determined as follows.

Eleven microliters of the sample is combined with 440 microliters of transfer solution (volume-to volume ratio of sample to admixture=1:41). The admixture is then contacted with electrodes capable of selectively sensing sodium, potassium, chloride, and calcium ions, respectively. Readings from each electrode are collected in millivolts and then converted to concentration values using standard techniques.

After the sample readings have been taken, the admixture is removed, and the electrodes are then contacted as above with the reference solution in order to provide sample reading reference values.

Other embodiments are within the following claims.

I claim:

1. A method for determining the concentrations of total calcium and least one monovalent ion in a sample which may contain protein bound calcium, comprising the steps of admixing said sample with a diluent, said diluent comprising 2 amino 2 hydroxymethyl-1,3-propanediol phosphate, said diluent having a pH within the range pH 6.5 to pH 7.0, said diluent being free of said monovalent ion, said admixing forming a diluted sample in which any said protein bound calcium in said sample is rendered detectable by a calcium specific ion selective electrode that is brought into contact with said diluted sample, contacting an aliquot of said diluted sample with a calcium specific ion selective electrode and an ion selective electrode specifically responsive to said monovalent ion, measuring the response of said calcium specific ion selective electrode as an indication of the concentration of total calcium in said sample, and measuring the response of said monovalent ion specific ion selective electrode as an indication of the concentration of said monovalent ion in said sample.

2. The method of claim 1 wherein said monovalent ion is sodium, potassium, or chloride.

3. The method of claim 1 wherein said diluent further comprises a reducing agent.

4. The method of claim 3 wherein said reducing agent is an aldehyde.

5. The method of claim 1 wherein said diluent further comprises a surfactant.

6. The method of claim 5 wherein said surfactant is a non ionic surfactant.

7. The method of claim 1 and further including the step of contacting said calcium specific ion selective electrode and said ion selective electrode specifically responsive to said monovalent ion with a reference solution that has the same chemical composition as said diluent except that said reference solution also contains calcium ion and said monovalent ion sources.

8. The method of claim 1 wherein the volume to volume ratio of said sample to said diluent is between 1:30 and 1:60.

9. The method of claim 1 wherein the concentration of said 2-amino-2-hydroxymethyl-1,3-propanediol phosphate in said diluent is at least 0.1 millimol per liter.

10. The method of claim 1 wherein the concentration of said 2-amino-2-hydroxymethyl-1,3-propanediol phosphate in said diluent is between 0.1 and 0.2 millimol per liter.

11. The method of claim 1 wherein chloride-specific, sodium specific and potassium specific ion selective electrodes are contacted with said aliquot of diluted sample concurrently with the contacting of aliquot of diluted sample with said calcium-specific ion selective electrode.

12. A method for determining the concentration of calcium, chloride, sodium, and potassium in a sample of a biological fluid which may contain protein-bound calcium, comprising the steps of (a) admixing said sample with a diluent, said diluent comprising 2-amino-2-hydroxymethyl-1,3-propanediol phosphate, said diluent having a pH within the range pH 6.5 to pH 7.0, said diluent being free of ions of calcium, sodium, potassium, and chloride, said admixing forming a diluted sample in which any said protein bound calcium in said sample is rendered detectable by a calcium-specific ion selective electrode that is brought into contact with said diluted sample, (b) contacting an aliquot of said diluted sample with a calcium-specific ion selective electrode, said calcium specific ion selective electrode comprising a calcium ionophore capable of selectively binding calcium ions, (c) measuring the response of said calcium specific ion selective electrode as an indication of the concentration of total calcium in said sample, (d) contacting said aliquot with a chloride specific ion selective electrode, (e) measuring the response of said chloride specific ion selective electrode as an indication of the concentration of chloride in said sample, (f) contacting said aliquot with a sodium specific ion selective electrode, (g) measuring the response of said sodium-specific ion selective electrode as an indication of the concentration of sodium in said sample, (h) contacting said aliquot with a potassium-specific ion selective electrode, and (i) measuring the response of said potassium-specific ion selective electrode as an indication of the concentration of potassium in said sample.

13. The method of claim 12 wherein said contacting steps (b), (d), (f) and (h) are performed concurrently.

14. The method of claim 12 wherein said diluent further comprises a reducing agent and a surfactant.

15. The method of claim 14 wherein said reducing agent is an aldehyde and said surfactant is a non ionic surfactant.

16. The method of claim 12 further comprising the steps of (j) contacting said ion selective electrodes with an aliquot of a reference solution, said reference solution comprising 2-amino-2-hydroxymethyl-1,3-propanediol phosphate and known concentrations of the ions of each of calcium, sodium, chloride, and potassium, and (k) measuring the response of said selective electrodes to said known concentrations of said ions as a calibration of said electrodes.

17. The method of claim 16 wherein each of said diluent and said reference solution further comprises a reducing agent and a surfactant.

18. The method of claim 17 wherein said reducing agent is an aldehyde and said surfactant is a non-ionic surfactant.

19. The method of claim 18 wherein the volume to volume ratio of said sample to said diluent is between 1:30 and 1:60.

20. The method of claim 19 wherein the concentration of said 2-amino-2-hydroxymethyl-1,3-propanediol phosphate in said diluent is at least 0.1 millimol per liter.

21. The method of claim 20 wherein the concentration of said 2-amino-2-hydroxymethyl-1,3-propanediol phosphate in said diluent is between 0.1 and 0.2 millimol per liter.

* * * * *